United States Patent
Shrawat et al.

(10) Patent No.: US 9,732,030 B2
(45) Date of Patent: Aug. 15, 2017

(54) PROCESS FOR THE PREPARATION OF FINGOLIMOD AND ITS SALTS

(71) Applicant: SHILPA MEDICARE LIMITED, Raichur (IN)

(72) Inventors: Vimal Kumar Shrawat, Raichur (IN); Rafiuddin Dr, Raichur (IN); Akshaykant Chaturvedi, Vizianagaram (IN)

(73) Assignee: SHILPA MEDICARE LIMITED, Karnataka (IN)

( * ) Notice: Subject to any disclaimer, the term of this patent is extended or adjusted under 35 U.S.C. 154(b) by 0 days.

(21) Appl. No.: 14/759,224

(22) PCT Filed: Jan. 11, 2014

(86) PCT No.: PCT/IB2014/058192
§ 371 (c)(1),
(2) Date: Jul. 4, 2015

(87) PCT Pub. No.: WO2014/111836
PCT Pub. Date: Jul. 24, 2014

(65) Prior Publication Data
US 2015/0344409 A1    Dec. 3, 2015

(30) Foreign Application Priority Data
Jan. 17, 2013 (IN) .............................. 223/CHE/2013

(51) Int. Cl.
*C07C 213/00* (2006.01)
*C07C 231/12* (2006.01)

(52) U.S. Cl.
CPC .......... *C07C 213/00* (2013.01); *C07C 231/12* (2013.01); *C07B 2200/13* (2013.01)

(58) Field of Classification Search
None
See application file for complete search history.

(56) References Cited

U.S. PATENT DOCUMENTS 5,604,229 A    2/1997    Fujita et al.

FOREIGN PATENT DOCUMENTS

| JP | 40-79505T B2 | 4/2008 |
| WO | 0027798 A1 | 5/2000 |

(Continued)

OTHER PUBLICATIONS

JP4079505 machine translation from 2016.*

(Continued)

*Primary Examiner* — Clinton Brooks

(57) ABSTRACT

The present invention provides process for preparation of Fingolimod hydrochloride (I).

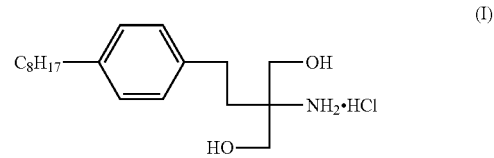

(I)

Fingolimod hydrochloride (I) as Form-β obtained by the process of present invention may be useful as active pharmaceutical ingredient in pharmaceutical compositions for the treatment of autoimmune related disorder including multiple sclerosis.

4 Claims, 4 Drawing Sheets

(56) References Cited

FOREIGN PATENT DOCUMENTS

| WO | 2010055028 A2 | 5/2010 |
| WO | 2012056458 A2 | 5/2012 |
| WO | 2012070059 A1 | 5/2012 |
| WO | 2012146980 A2 | 11/2012 |

OTHER PUBLICATIONS

Bhaskar et al; "Practical synthesis of Fingolimod from diethyl acetamidemalonate"; RSC Advances, vol. 3, Issue 25, pp. 9687-9689.

\* cited by examiner

PROCESS FOR THE PREPARATION OF FINGOLIMOD AND ITS SALTS

The following specification particularly describes the invention and the manner in which it is to be performed.

FIELD OF THE INVENTION

The present invention provides process for preparation of Fingolimod hydrochloride (I).

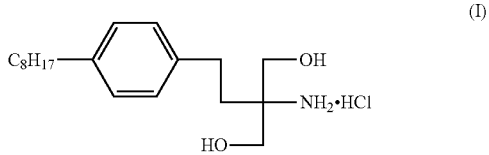

Fingolimod hydrochloride (I) as Form-β obtained by the process of present invention may be useful as active pharmaceutical ingredient in pharmaceutical compositions for the treatment of autoimmune related disorder including multiple sclerosis.

INTRODUCTION

Fingolimod hydrochloride has the IUPAC name as 2-amino-2-[2-(4-octylphenyl)ethyl]propane-1,3-diol hydrochloride and has the following structure:

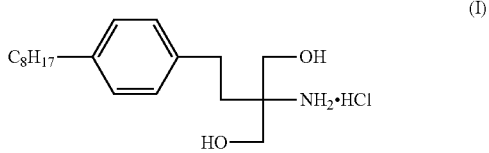

It is a structural analogue of sphingosine (II) which gets phosphorylated by sphingosine kinases in the cell (specifically sphingosine kinase 2).

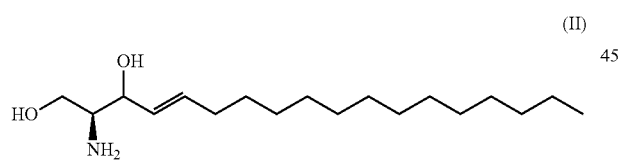

Fingolimod being a sphingosine 1-phosphate receptor (S1P-R) modulator, it binds to the S1P receptor on circulating lymphocytes, sequestering them in lymph nodes away from the CNS. It appears to be the first oral S1P-R modulator to be developed, which appears to reduce the number of inflammatory T cells in the circulation and CNS and in doing so it reduces their potential to damage nerve cells.

U.S. Pat. No. 5,604,229 is the first disclosure of the Fingolimod, its processes and other related compounds. It has been found to be useful in the treatment or prevention of various autoimmune conditions, including multiple sclerosis.

Mutz et al in WO2010055028A2 reported various polymorphic forms of Fingolimod hydrochloride designated as Form-I (at room temperature), Form-II (however at a transition temperature of approximately 40° C.) and Form-III (however at a transition temperature of approximately 66° C.).

Shrawat et al in PCT application WO2012070059A1 further disclosed three different crystalline forms of Fingolimod hydrochloride designated as Form α, Form β and Form μ along with the processes for preparation thereof. Inventors of the present application observed that Form β appears to be highly stable form and has further characteristic features, which are detailed herein below in the description of present application.

Further, in view of the existence of various literature/information known for processes related to preparation of Fingolimod hydrochloride, there stills appears to be a need of process/es, which are not only economically viable but also amenable to scale up and provide improved yields & quality. Thus, the inventors of the present application in one of the embodiment provide a process for preparation of Fingolimod hydrochloride (I) or its other pharmaceutically acceptable salts.

SUMMARY OF INVENTION

Particular aspects of the present application relate to the process/es for preparation of Fingolimod and its salts. The application further relates to processes for preparation of Fingolimod HCl (I) and its stable crystalline polymorphic Form-β, which is substantially free from process related impurities. The crystalline polymorphic Form-β of Fingolimod HCl (I) obtained by the process according to the present invention is useful as active pharmaceutical ingredient in pharmaceutical compositions for the treatment of autoimmune related disorders including multiple sclerosis. Different aspects of the present application are summarized herein below individually.

In one aspect of the present application, the present invention provides process for preparation of Fingolimod hydrochloride (I)

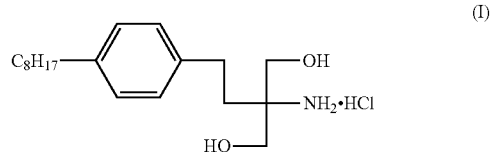

comprising the steps of—
a. reacting 2-acetamido1,3-diacetoxy-2-(2-phenylethyl)propane (A) with octanoyl chloride (B) in mole ratio ranging between 2 to 6 Moles with respect to (A) in presence of a Friedel-Craft's catalyst and a halohydrocarbon organic solvent under inert atmosphere to form 2-acetamido-2-(4-octanoylphenethyl)propane-1,3-diyl diacetate (C);

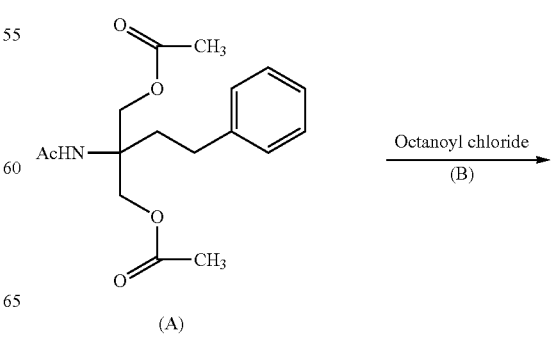

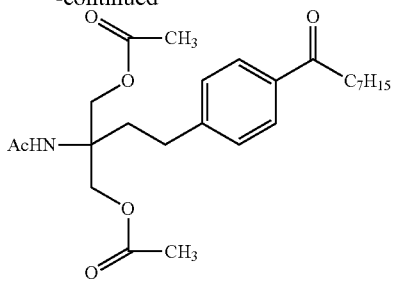

(C)

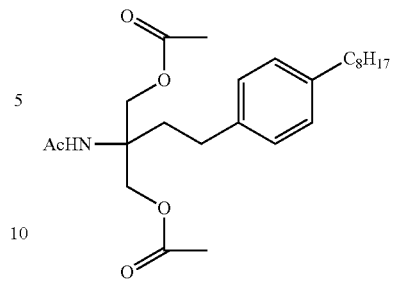

(D)

b. selectively hydrogenating 2-acetamido-2-(4-octanoylphenethyl)propane-1,3-diyl diacetate (C) at temperature ranging between 20-35° C. to get 2-acetamido-2-(4-octylphenethyl)propane-1,3-diyl diacetate (D);

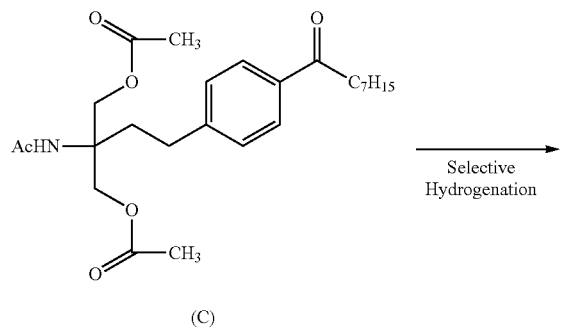

(C)

Selective Hydrogenation →

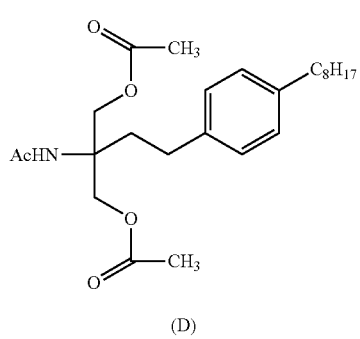

(D)

c. optionally recrystallizing the product obtained in step b. with hydrocarbon solvent or an alcoholic solvent or both, to get pure 2-acetamido-2-(4-octyl phenethyl) propane-1,3-diyl diacetate (D);

d. treating 2-acetamido-2-(4-octylphenethyl)propane-1,3-diyl diacetate (D) in the presence of organic solvents selected from $C_1$-$C_4$ alcohol and a base to get Fingolimod free base (E);

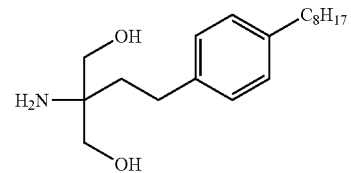

(E)

e. converting Fingolimod free base (E) into Fingolimod hydrochloride (I) in an organic solvent and 5 to 15% w/w IPA-HCl solution at pH ranging between 1.00 to 3.00.

In another aspect of the present application, the present invention provides the process for preparation of Fingolimod HCl (I) stable crystalline polymorphic Form-β, which is substantially free from process related impurities and is characterized by X-ray powder diffraction pattern having characteristic 2θ° peaks in XRPD peak set of 3.54, 7.10, 10.67, 15.36, 17.83, 20.53, 21.49, 23.29, 25.12, 26.68 and 29.22±0.1 2θ°; un-split peak near at 20.5 2θ° and DSC isotherm comprising endothermic peaks selected from Peak-1: ranging between 40 to 45° C., Peak-2: ranging between 65 to 70° C. and Peak-3: ranging between 107 to 115° C.

A further aspect of the present application provides Fingolimod hydrochloride (I) crystalline Form-β having particle size distribution obtained by dispersing in light liquid paraffin, characterized by d(0.1): 10-20 μm; d(0.5): 25-35 μm and d(0.9): 45-65 μm.

In further aspect, the Crystalline Form-β of Fingolimod HCl obtained by the process of the present application may be formulated as solid compositions for oral administration in the form of capsules, tablets, pills, powders or granules useful in the treatment of autoimmune related disorder including multiple sclerosis.

DETAILED DESCRIPTION

As set forth herein, embodiments of the present invention relate to a process for preparation of Fingolimod HCl (I) and its stable crystalline polymorphic Form-β, which is substantially free from process related impurities. Individual embodiments of the present invention are detailed herein below separately.

In one embodiment of the present application, it provides a process for preparing Fingolimod HCl (I) crystalline polymorphic Form-β

Figure 1:
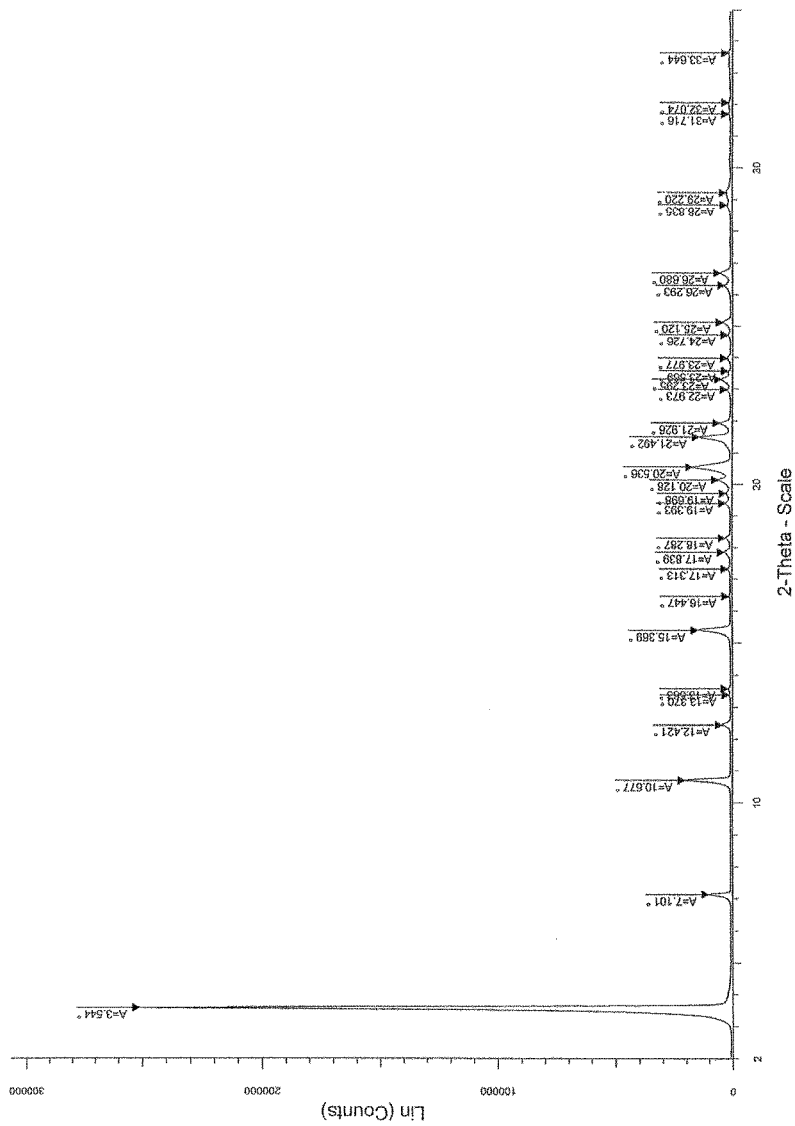
FIG. 1 is an illustration of X-ray powder diffraction (XRPD) pattern of Fingolimod hydrochloride—Form β obtained according to process of Example-1.
Figure 2:
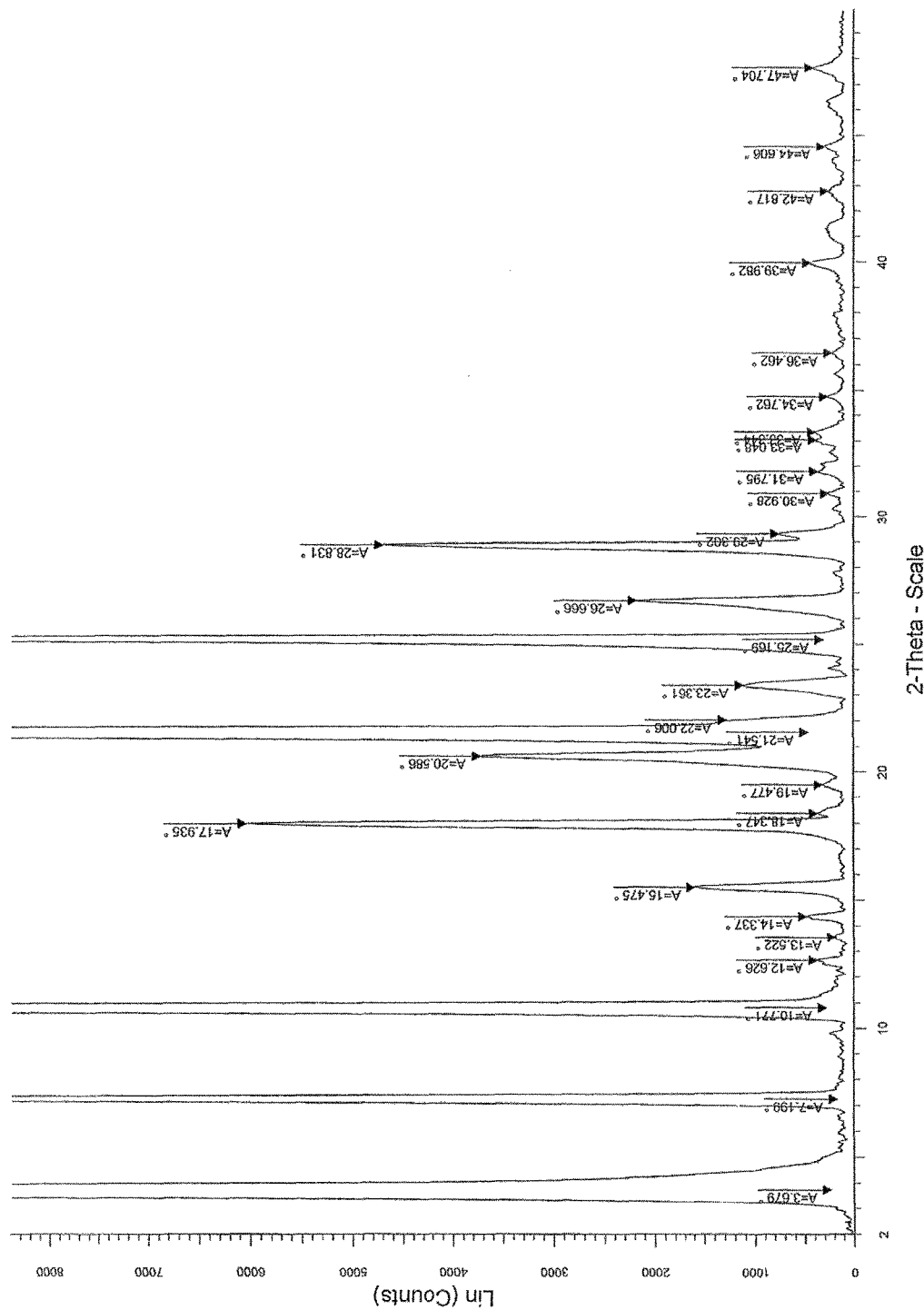
FIG. 2 is an illustration of X-ray powder diffraction (XRPD) pattern of Fingolimod hydrochloride—Form β obtained according to process of Example-2.
Figure 3:
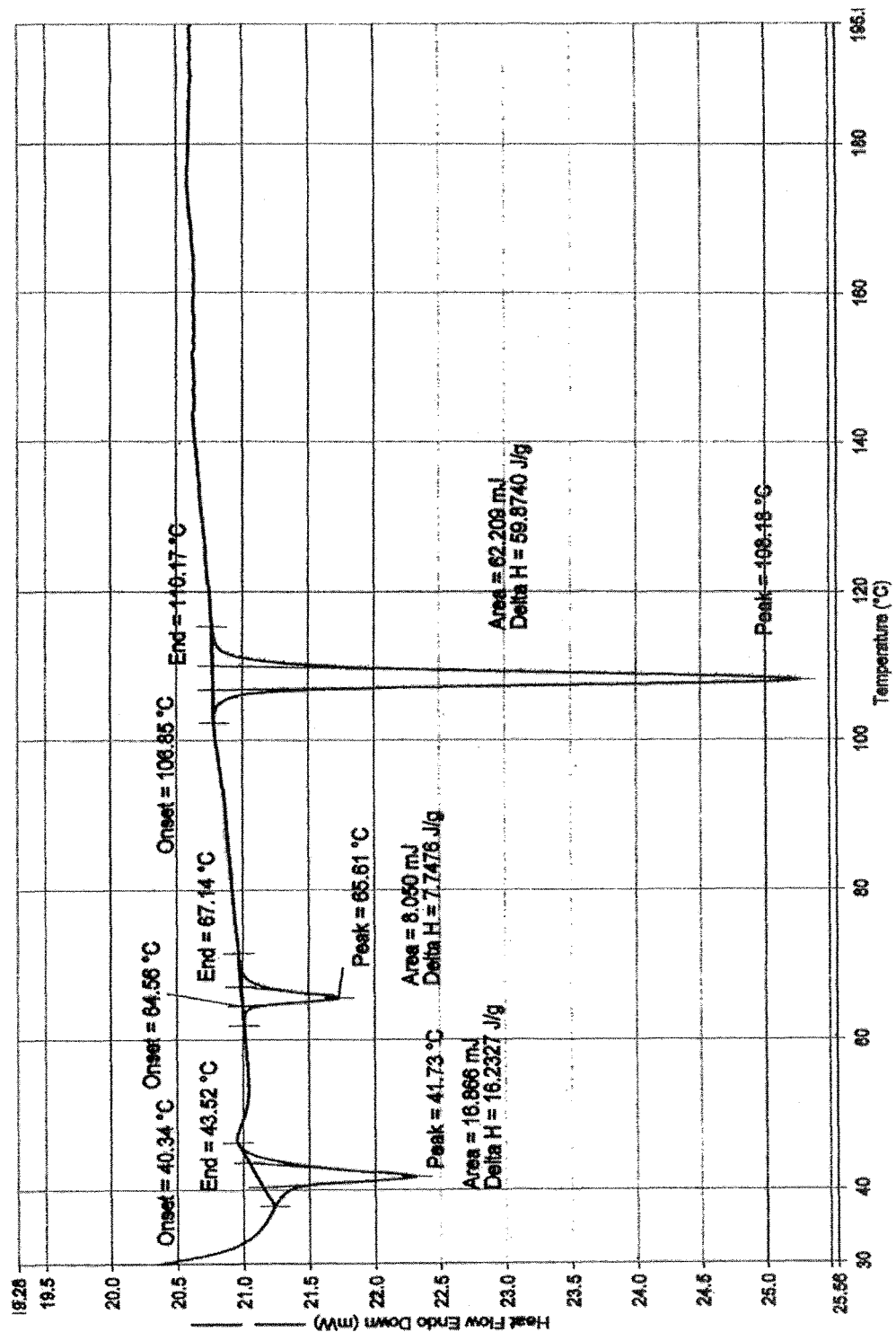
FIG. 3 is an illustration of a differential scanning calorimetric ("DSC") curve of Fingolimod hydrochloride—Form β.
Figure 4:
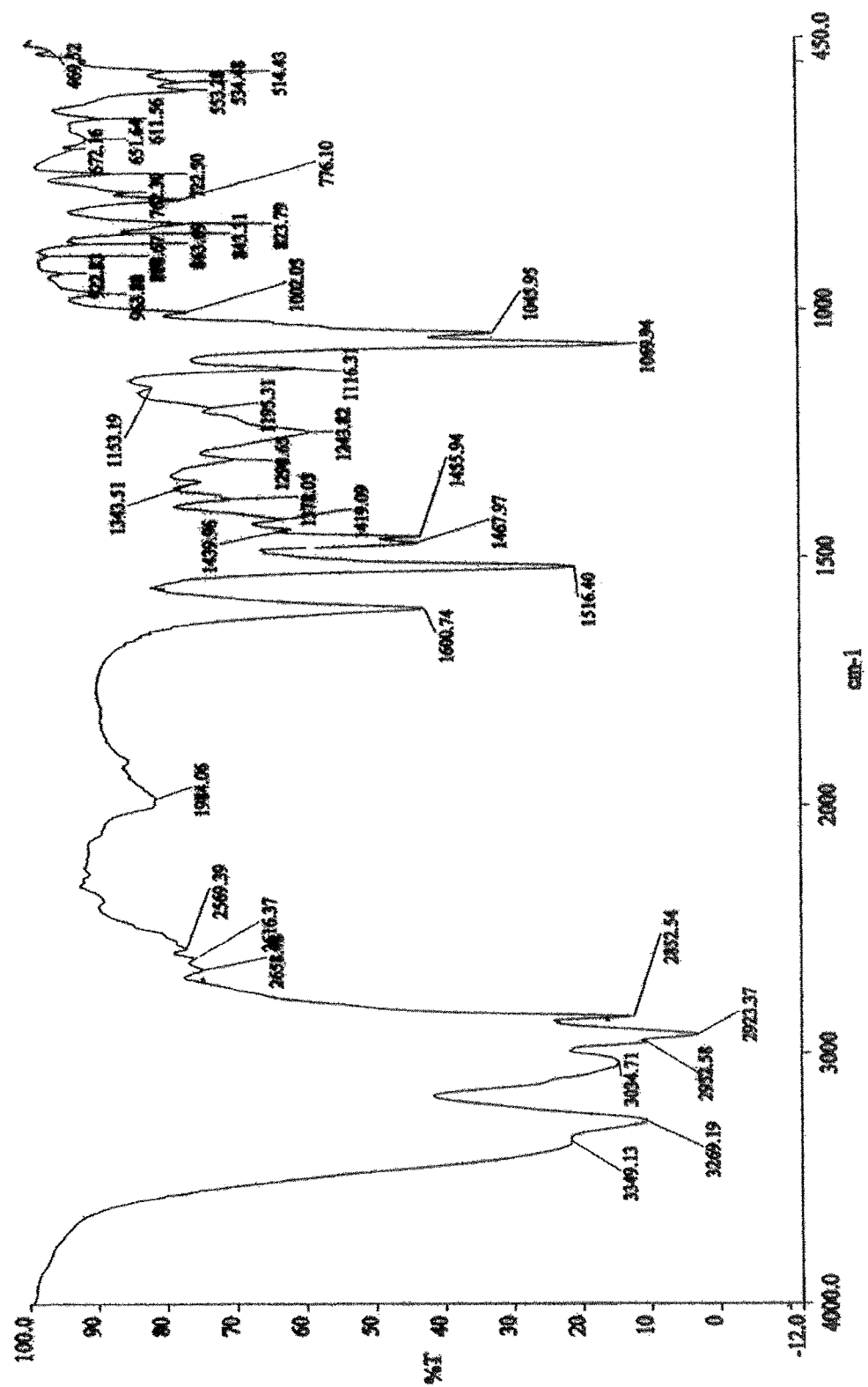
FIG. 4 is an illustration of IR spectrum of Fingolimod hydrochloride—Form β.

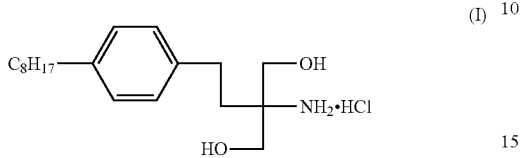

characterized by X-ray powder diffraction pattern as per FIG. 1 or FIG. 2, DSC curve as per FIG. 3 and IR spectrum as per FIG. 4.

In another embodiment of the present application, it provides a process for preparing Fingolimod HCl (I) crystalline polymorphic Form-β characterized by X-ray powder diffraction pattern having characteristic 2θ° peaks in XRPD peak set of 3.54, 7.10, 10.67, 15.36, 17.83, 20.53, 21.49, 23.29, 25.12, 26.68 and 29.22±0.1 2θ°; un-split peak near at 20.5 2θ° and DSC isotherm comprising endothermic peaks selected from Peak-1: ranging between 40 to 45° C., Peak-2: ranging between 65 to 70° C. and Peak-3: ranging between 107 to 115° C.

In still another embodiment of the present application, it provides a process for preparing Fingolimod HCl (I) crystalline polymorphic Form-β characterized by X-ray powder diffraction pattern having characteristic 2θ° peaks in XRPD peak set of 3.54, 7.10, 10.67, 15.36, 20.53, 21.49 and 25.12±0.1 2θ° and DSC isotherm comprising endothermic peaks selected from Peak-1: ranging between 40 to 45° C., Peak-2: ranging between 65 to 70° C. and Peak-3: ranging between 107 to 115° C.

In a further embodiment of the present application, it provides a process for preparing Fingolimod HCl (I) crystalline polymorphic Form-β, which is further characterized by:
  i. X-ray powder diffraction pattern comprising an un-split peak near at 20.5 2θ°;
  ii. Other characteristic 2θ° peaks selected from the XRPD peak set of 17.83, 23.29, 26.68 and 29.22±0.1 2θ°.

Crystalline polymorphic Form-β prepared by the process of the present invention is also characterized by having particle size distribution obtained by dispersing in light liquid paraffin, having particle size distribution substantially as d(0.1): 10-20 μm; d(0.5): 25-35 μm and d(0.9): 45-65 μm.

In an embodiment of the present application, it provides a process for preparation of Fingolimod hydrochloride (I), comprising the steps of—
  a. reacting 2-acetamido1,3-diacetoxy-2-(2-phenylethyl) propane (A) with octanoyl chloride (B) in mole ratio ranging between 2 to 6 Moles with respect to (A) in presence of a Friedel-Craft's catalyst and a halohydrocarbon organic solvent under inert atmosphere to form 2-acetamido-2-(4-octanoylphenethyl)propane-1,3-diyl diacetate (C);
  b. selectively hydrogenating 2-acetamido-2-(4-octanoylphenethyl)propane-1,3-diyl diacetate (C) at temperature ranging between 20-35° C. to get 2-acetamido-2-(4-octylphenethyl)propane-1,3-diyl diacetate (D);
  c. optionally recrystallizing the product obtained in step b. with hydrocarbon solvent or an alcoholic solvent or both, to get pure 2-acetamido-2-(4-octyl phenethyl) propane-1,3-diyl diacetate (D);
  d. treating 2-acetamido-2-(4-octylphenethyl)propane-1,3-diyl diacetate (D) in the presence of organic solvents selected from $C_1$-$C_4$ alcohol and a base to get Fingolimod free base (E);
  e. converting Fingolimod free base (E) into Fingolimod hydrochloride (I) in an organic solvent and 5 to 15% w/w IPA-HCl solution at pH ranging between 1.00 to 3.00.

The individual steps of the process according to the present invention for preparing Fingolimod hydrochloride (I) are detailed separately herein below.

Step a. comprises reacting 2-acetamido1,3-diacetoxy-2-(2-phenylethyl)propane (A) with octanoyl chloride (B) in mole ratio ranging between 2 to 6 Moles with respect to (A) in presence of a Friedel-Craft's catalyst and a halohydrocarbon organic solvent under inert atmosphere to form 2-acetamido-2-(4-octanoylphenethyl)propane-1,3-diyl diacetate (C);

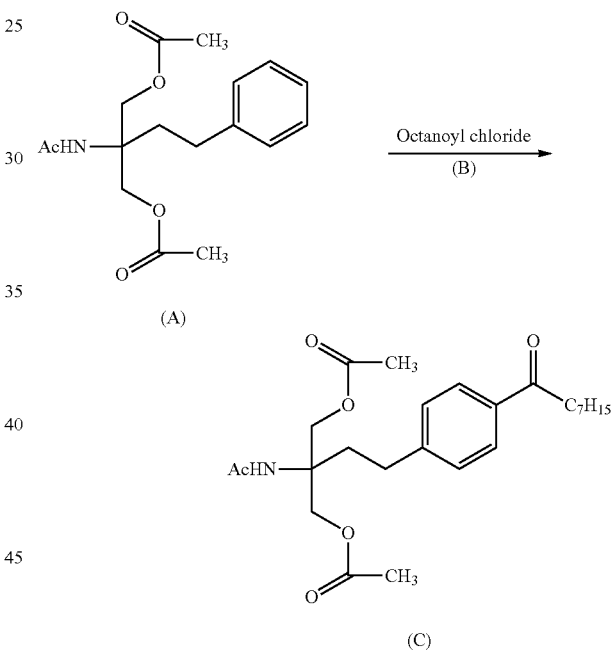

The amount of octanoyl chloride (B) used for the present reaction (in mole ratio) ranges between 2 to 6 Moles with respect to 2-acetamido1,3-diacetoxy-2-(2-phenylethyl)propane (A). In one particular embodiment for 0.5 moles of 2-acetamido1,3-diacetoxy-2-(2-phenylethyl)propane, 1.88 moles of ocatanoyl chloride were used. Besides octanoyl chloride; octanoyl bromide or octanoyl anhydride can also be used in this reaction for the introduction of octanoyl group onto the benzene ring of reactant A.

Halohydrocarbon solvent in the present reaction may be selected from dichloromethane, dichloroethane or chloroform. Friedel-Craft's catalyst used in this step may be a Lewis acid which may further be selected from $FeCl_3$, $AlCl_3$, $TiCl_4$, $ZnCl_2$ or $BF_3$. Amount of Friedel-Craft's catalyst used in this reaction ranges between 2 to 6 times by weight with respect to the weight of 2-acetamido1,3-diacetoxy-2-(2-phenylethyl)propane (A) used.

Inert atmosphere to be utilized for the conduct of the present reaction may be suitably chosen by a person skilled in the art, according to the methods provided in literature. For e.g. a non-limiting illustration of inert atmosphere can be nitrogen atmosphere.

Addition of 2-acetamido1,3-diacetoxy-2-(2-phenylethyl) propane to a solution of octanoyl chloride in Halohydrocarbon solvent in presence of a Friedel-Craft's catalyst is done slowly at a temperature ranging between −5 to 10° C. This is followed by slowly allowing the temperature of reaction mass to rise to a temperature between 18-25° C. which is maintained (under stirring) for time duration of 3-20 hours depending upon the progress of the reaction.

2-acetamido-2-(4-octanoylphenethyl)propane-1,3-diyl diacetate (C) obtained in this step is optionally purified by using column chromatography or by giving treatment with organic solvent like hexane, to achieve the desired purity levels.

Step b. comprises selectively hydrogenating 2-acetamido-2-(4-octanoylphenethyl)propane-1,3-diyl diacetate (C) at temperature ranging between 20-35° C. to get 2-acetamido-2-(4-octylphenethyl)propane-1,3-diyl diacetate (D);

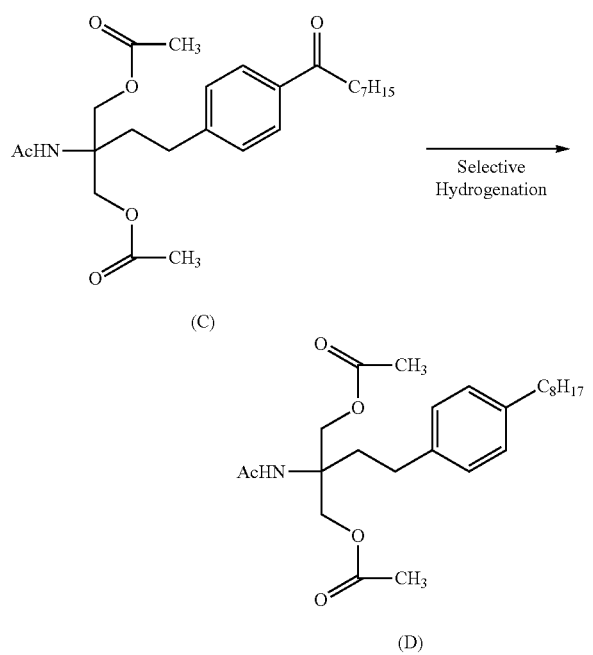

Selective hydrogenation conditions used is this reaction may be chosen from suitable reagents/conditions known in the prior art. In one of the preferred embodiments the reducing agent used in this step of the present invention is 10% Pd/C, which is used up to an amount 0.1-0.5 gm per gm of reactant (C). Use of 10% Pd/C is done along with purging of Hydrogen gas into the reaction mixture which is maintained at ambient temperature for time duration of 3 to 14 hours depending upon the progress of the reaction. Optionally, purging of Hydrogen gas may also be performed by maintaining the pressure of 4-4.5 Kg/cm². As described earlier, other methods of reduction known in the prior art for e.g. clemmensen reduction, birch reduction, use of hydrosilanes, Raney Nickel can also be suitably employed for the transformation involved in this step.

Step c. comprises optionally recrystallizing the product obtained in step b. with hydrocarbon solvent or an alcoholic solvent or both, to get pure 2-acetamido-2-(4-octyl phenethyl) propane-1,3-diyl diacetate (D);

Hydrocarbon solvent used for the recrystallization of the intermediate D in this step can be selected from n-hexane, n-heptane or a mixture thereof. Recrystallization step is carried out at a temperature ranging between −5 to +8° C.

Intermediate D obtained in the present reaction or reaction of step b. can optionally be purified further by treatment with alcoholic solvent like methanol, ethanol or a mixture thereof, at temperature ranging between −5 to +5° C. to afford the material of desired purity. In case required, this step of treatment with alcoholic solvent may be repeated till the required purity is obtained.

Step d. comprises treating 2-acetamido-2-(4-octylphenethyl) propane-1,3-diyl diacetate (D) in the presence of organic solvents selected from $C_1$-$C_4$ alcohol and a base to get Fingolimod free base (E);

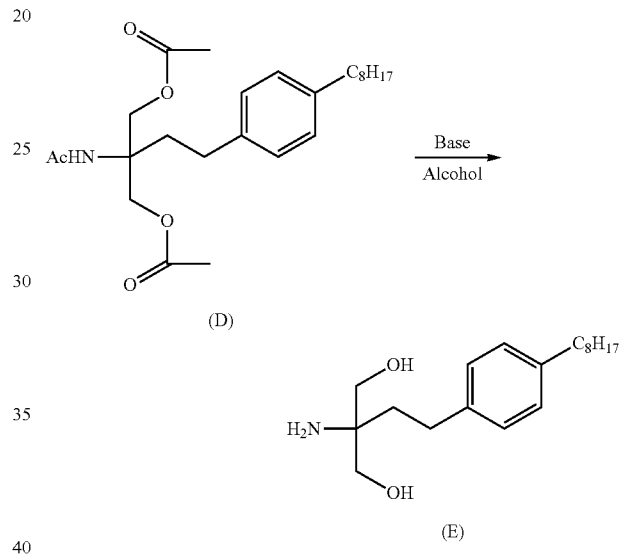

$C_1$-$C_4$ alcohol solvent used in the present step may be selected from methanol, ethanol or isopropanol and is used up to at least 12 to 20 times (by volume) with respect to the weight of compound D. In one of the particular embodiment, 2250 ml methanol is used for 150 g 2-acetamido-2-(4-octylphenethyl)propane-1,3-diyl diacetate (D).

Alkali metal hydroxide used in the present step may be selected from LiOH, NaOH, KOH or a hydrate form thereof, and is used up to 2-3 times (by weight) with respect to the weight of compound D. Alkali metal hydroxides may optionally be used in the form of a solution with water.

The reaction of 2-acetamido-2-(4-octylphenethyl)propane-1,3-diyl diacetate (D) in the presence of C1-C4 alcohol and alkali metal hydroxide to get Fingolimod free base (E) is carried out at a temperature up to not less than 50° C., preferably under reflux conditions.

The free base form of Fingolimod can be extracted from the reaction mass using a suitable organic solvent like ethyl acetate, which can be removed from the final product by drying under reduced pressure at a temperature ranging between 40-50° C. for time duration of 5-8 hours. However, this time may be more, depending upon achieving equilibration to impurity profile compliance and drying achieved.

The Fingolimod free base obtained in this step can be further converted to a suitable pharmaceutically acceptable acid addition salt, wherein acid can be an organic acid like acetic acid, fumaric acid, methanesulfonic acid or benzenesulfonic acid or inorganic acid like HCl, HBr or sulphate. Step e. comprises converting Fingolimod free base (E) into Fingolimod hydrochloride (I) in an organic solvent and 5 to 15% w/w IPA-HCl solution at pH ranging between 1.00 to 3.00.

A solution of Fingolimod free base is provided with an ester or a halohydrocarbon organic solvent. Amount of organic solvent used in this reaction plays an important role in the progress of the reaction as well as the end product achieved. Organic solvent used is used in the range of up to more than 20 times (by volume) but less than 50 times (by volume) with respect to weight of Fingolimod free base. Non-limiting examples of ester solvent used in this reaction include ethyl acetate, methyl acetate or isopropyl acetate and non-limiting examples of halohydrocarbon solvent include dichloromethane or dichloroethane. Any form of Crude or Pure Fingolimod obtained by processes known in prior art can also be used in the present reaction for preparation of Fingolimod hydrochloride.

To the solution of Fingolimod free base in organic solvent, optionally activated Carbon may be added to get rid of unwanted impurities, which may be followed by filtration. IPA-hydrochloric acid solution of strength 5 to 15% w/w is added to the solution of Fingolimod free base at pH ranging between 1.00 to 3.00 at a temperature up to not less than 35° C., preferably under reflux conditions to convert free base form to its acid addition salt. The final end product is obtained by slowly cooling the reaction mass to a temperature ranging between −5 to +5° C., which is maintained for time duration ranging between 1-5 hours depending upon the reaction progress, thereby obtaining the crystalline material which can be optionally given washing with a suitable solvent like ethyl acetate or DCM followed by drying at raised temperature of 40-50° C. under reduced pressure conditions.

The product may be isolated from the reaction mass by conventional processes including filtering and optional drying, which may be carried out at room temperature for the suitable durations to retain the crystalline polymorphic form characteristics.

The crystalline final product obtained is characterized by X-ray powder diffraction pattern substantially according to FIG. 1 or FIG. 2, DSC isotherm according to FIG. 3 and IR according to FIG. 4, thereby confirming that the Fingolimod hydrochloride obtained as final end product is Fingolimod hydrochloride crystalline Form-β.

Final Fingolimod hydrochloride crystalline Form-β, obtained by the process of the present invention has well defined particle size distribution, thus providing advantage of ease in further processing of the API. Particle size distribution of the Fingolimod hydrochloride crystalline Form-β obtained by the process of the present invention is characterized by d(0.1): 10-20 μm; d(0.5): 25-35 μm and d(0.9): 45-65 μm as obtained by dispersion in light liquid paraffin.

The merit of the process according to the present invention resides in that—product obtained after recovery is directly obtained in crystalline Form-β, with consistency in regular production batches. Said material was found to be adequately stable to handle and store for longer time (at least up to more than 6 months) without any significant or measurable change in its morphology and physicochemical characteristics.

The process related impurities, including unreacted intermediates, side products, and other medium dependent impurities, that appears in the impurity profile of the Fingolimod hydrochloride can substantially be reduced by the process of the present invention resulting in the formation substantially pure crystalline form-β. A substantially pure product having purities more than 99% (by HPLC) can be obtained by the process of the present invention. In view of maintaining the equilibrium to the impurity profile compliance, the process may require regular quality checks.

The Crystalline Form-β of Fingolimod HCl described herein may be characterized by X-ray powder diffraction pattern (XRPD) and Thermal techniques such as differential scanning calorimetric (DSC) Analysis. The samples of Fingolimod HCl Crystalline Form-β were analyzed by XRPD on a Bruker D8 Advance Diffractometer using X-ray source—Cu Kα radiation using the wavelength 1.5418 Å, however, DSC analysis were carried out on a Perkin Elmer Jade instrument. Illustrative examples of analytical data for the crystalline solids Form-β obtained in the Examples are set forth in the FIGS. 1-4.

In another embodiment, the Crystalline Form-β of Fingolimod HCl obtained by the processes of the present application may be formulated as solid compositions for oral administration in the form of capsules, tablets, pills, powders or granules useful in the treatment or prevention of autoimmune related disorder including multiple sclerosis. In these compositions, the active product is mixed with one or more pharmaceutically acceptable excipients. The drug substance can be formulated as liquid compositions for oral administration including solutions, suspensions, syrups, elixirs and emulsions, containing solvents or vehicles such as water, sorbitol, glycerine, propylene glycol or liquid paraffin.

The compositions for parenteral administration can be suspensions, emulsions or aqueous or non-aqueous sterile solutions. As a solvent or vehicle, propylene glycol, polyethylene glycol, vegetable oils, especially olive oil, and injectable organic esters, e.g. ethyl oleate, may be employed. These compositions can contain adjuvants, especially wetting, emulsifying and dispersing agents. The sterilization may be carried out in several ways, e.g. using a bacteriological filter, by incorporating sterilizing agents in the composition, by irradiation or by heating. They may be prepared in the form of sterile compositions, which can be dissolved at the time of use in sterile water or any other sterile injectable medium.

Pharmaceutically acceptable excipients used in the compositions comprising Crystalline Form-β of Fingolimod HCl obtained by the process of the present invention include, but are but not limited to diluents such as starch, pregelatinized starch, lactose, powdered cellulose, microcrystalline cellulose, dicalcium phosphate, tricalcium phosphate, mannitol, sorbitol, sugar and the like; binders such as acacia, guar gum, tragacanth, gelatin, pre-gelatinized starch and the like; disintegrants such as starch, sodium starch glycolate, pregelatinized starch, Croscarmellose sodium, colloidal silicon dioxide and the like; lubricants such as stearic acid, magnesium stearate, zinc stearate and the like; glidants such as colloidal silicon dioxide and the like; solubility or wetting enhancers such as anionic or cationic or neutral surfactants, waxes and the like. Other pharmaceutically acceptable excipients that are of use include but not limited to film formers, plasticizers, colorants, flavoring agents, sweeteners, viscosity enhancers, preservatives, antioxidants and the like.

Pharmaceutically acceptable excipients used in the compositions derived from Crystalline Form-β of Fingolimod HCl obtained by the process of the present invention may also comprise to include the pharmaceutically acceptable carrier used for the preparation of solid dispersion, wherever utilized in the desired dosage form preparation.

Certain specific aspects and embodiments of the present application will be explained in more detail with reference to the following examples, which are provided by way of illustration only and should not be construed as limiting the scope of the invention in any manner.

EXAMPLE

The process for preparation of Fingolimod hydrochloride crystalline Form-β according to the present invention is a multistep procedure which is detailed in the stepwise demonstration mentioned herein below:

Reference Example

Preparation of 2-acetamido-2-phenethylpropane-1,3-diyl diacetate

Step 1. Preparation of Diethyl-2-acetamido-2(2-phenyl ethyl) malonate

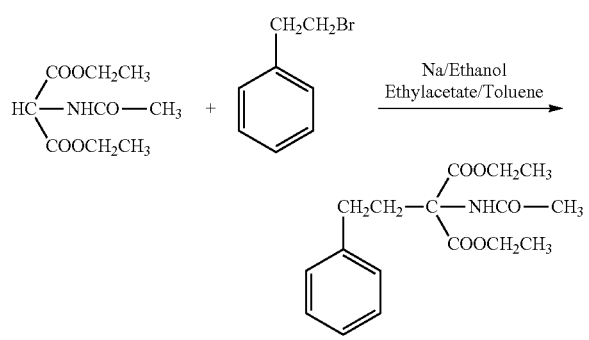

Ethyl alcohol (5.12 Lit) was charged in a four necked RB flask and heated up to 50° C. Further Sodium metal was added slowly in six lots under stirring in 2-3 hours to get the clear solution. The reaction temperature was then cooled to RT under stirring. In to the freshly prepared sodium ethoxide solution 1.0 kg diethyl acetamido malonate was added and stirred for one hour. Then a solution of 1.14 kg 2-phenyl ethyl bromide dissolved in 3.5 liter ethyl alcohol was slowly added to the reaction mass in 2-3 hours along with continuous stirring. After the completion of this addition, the reaction was heated and temperature was slowly raised to reflux, which was maintained for 9-10 hours under stirring. After completion of the reaction as confirmed by HPLC, the reaction mixture was allowed to cool to room temperature and the reaction was decomposed by 10.0 lit chilled DM water.

The reaction mixture was then extracted by 5.0 lit ethyl acetate. Aqueous layer was also extracted with 1.0 lit ethyl acetate. Combined ethyl acetate layers were washed with 1.0 lit saturated brine solution and anhydrous sodium sulfate was added. Then Ethyl acetate was recovered under vacuum at temperature below 50° C. 250 ml Toluene was added to the reaction mass followed by cooling to 0-5° C. under stirring and maintaining this temperature for 2-3 hours. Solid material was separated, filtered and washed with 25 ml chilled toluene. The material obtained was dried at 40-45° C. under vacuum for 5-6 hours to afford 630.0 g title compound.

Step 2. Preparation of 2-acetamido-2-phenethylpropane-1,3-diyl diacetate

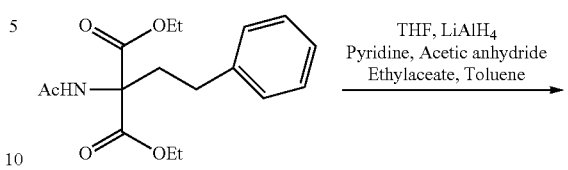

12.0 lit THF was added in a 20 lit RB Flask under nitrogen atmosphere under stirring and cooled to 0-5° C. Further 120.0 g Lithium Aluminium Hydride was slowly charged under stirring and stirred was continued for 30 mins. 400.0 g 2-acetamido-2-phenyl malonate dissolved in 2.4 lit of THF was added under stirring in one hour. During this addition, reaction temperature was slowly raised to about 10° C. along with continuous stirring. Reaction mixture was brought to RT where it was stirred for 2 hours. After checking the progress of the reaction by HPLC the reaction mixture was again cooled to 0-5° C. under stirring. Saturated sodium sulfate soln. (1200 ml) was slowly added to the reaction mass in one hour to decompose the lithium aluminum hydride (During this addition temperature rises up to 10° C. resulting in foaming nature of the reaction mixture). Reaction mixture was further stirred for 30 minutes. Then the reaction mixture is filtered and the solid cake obtained was washed with 1.0 Lit THF. THF was recovered at below 45° C. under vacuum to get a solid residue.

The residue obtained was dissolved in Pyridine (720 ml) and cooled to 0-5° C. Then acetic anhydride (560 ml) was added at RT under stirring. The reaction mixture was stirred for 12 hours. After checking the progress of reaction by HPLC, the reaction was decomposed by chilled DM Water (5.0 Lit) and the reaction mixture was extracted with Ethyl acetate (5.0 Lit). The aqueous layer was also extracted with Ethyl acetate (1.0 Lit). Combined Ethyl acetate layers were washed with saturated ammonium chloride soln. (3.0 Lit) and chilled water (1.0 Lit).

Anhydrous sodium sulfate is added to ethyl acetate layer. Then ethyl acetate layer is recovered below 50° C. under vacuum to get the solid residue. The residue was again dissolved in Toluene (200 ml) under stirring and cooled to 0-5° C. and this temperature was maintained for 2-3 hours. Separated solid material is filtered and dried under vacuum below 45° C. to get 125-130.0 g title compound.

Example 1

Preparation of Fingolimod hydrochloride (I)

Step-1: Preparation of 2-acetamido-2-(4-octanoylphenethyl)propane-1,3-diyl diacetate

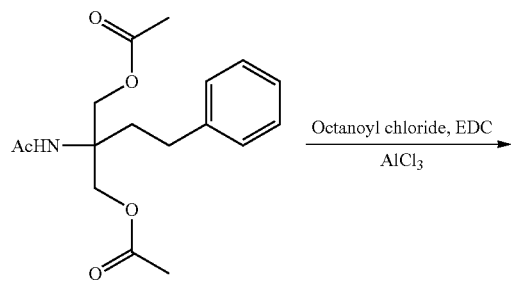

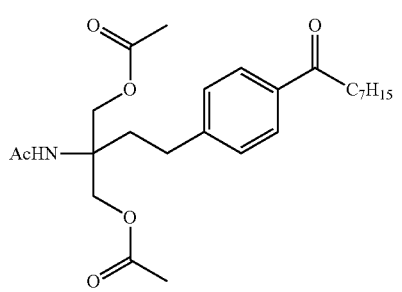

6.8 Lit EDC was charged in to three necked RB flask under nitrogen atmosphere and cooled to 0-5° C. 544.0 g Aluminum Chloride was added to the reaction setup and stirred for further 30 minutes. Octanoyl chloride (320.0 ml) was slowly added in to the reaction mixture in one hour under stirring. Then reaction mixture was brought to room temperature and stirred for two hours, followed by cooling to 0-5° C. 160.0 g 2-acetamido1,3-diacetoxy-2-(2-phenylethyl)propane dissolved in 480.0 ml EDC was slowly added to the reaction mixture under stirring in duration of two hours maintaining the temperature at 0-5° C. After addition, the reaction mixture was allowed to attain the temperature of 20-22° C. under stirring which was maintained for 5-6 hours. After completion of reaction as monitored by HPLC, reaction mixture was decomposed with chilled water (4.0 Lit). EDC layer was separated and the aqueous layer was again extracted with EDC (500 ml). EDC layer were combined and washed with saturated sodium chloride soln. (1.0 Lit). EDC layer was then separated and made moisture free by addition of anhydrous sodium sulfate (100.0 g). EDC layer was recovered under vacuum at temperature below 50° C. to get 320.0 g residue. The obtained residue was further purified by column chromatography over silica gel (230-400 mesh). The product was eluted with Ethyl acetate: Hexane (1:1). Appropriate fractions were combined and concentrated to get the residue. Further to this, hexane was added at RT to the residue under stirring which was continued for 30 minutes. The solid material was filtered and suck dried for 2-3 hours at RT to afford 96.0 g title compound.

Step-2: Preparation of 2-acetamido-2-(4-octylphenethyl)propane-1,3-diyl diacetate

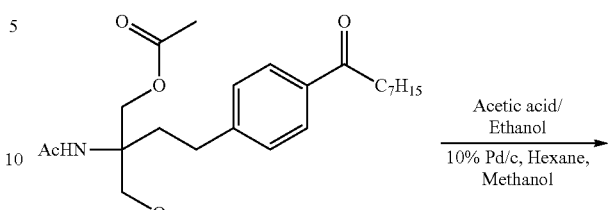

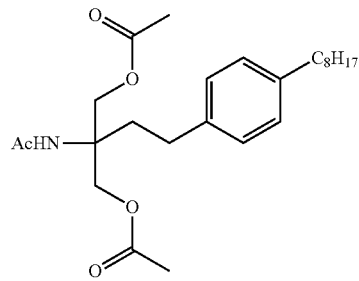

1800 ml Ethyl alcohol: Acetic acid (8:2), was charged in a three necked RB flask. 120.0 g of 2-acetamido-2-(4-octanoylphenethyl)propane-1,3-diyl diacetate was then added and stirred for 10-15 mints at room temperature till the solution becomes clear. This was followed by addition of 12.0 g 10% Pd/C under stirring. After this addition, Hydrogen gas was purged in to the reaction mixture under stirring and reaction was maintained for 4-5 hours at room temperature. After assessing the progress of the reaction by HPLC, the reaction mass was filtered with hyflow bed. The filtrate was then evaporated under full vacuum below 55° C. to get the residue. The residue was added to Hexane (240.0 ml) and stirred for 2-3 hours at 0-5° C. The separated solid material was filtered to afford 100 g crude title compound (HPLC purity=93.09%).

The obtained crude title compound was taken in methanol (1300 ml) and stirred for one hour to get the clear solution. The solution was then cooled to 0-5° C. under stirring which was maintained for two hours. The solid obtained was washed with chilled Methanol (150 ml), filtered and dried at 45° C. under vacuum for 2-3 hours, to obtain 80.0 g compound (HPLC purity=98.18%). This 80.0 g material was again dissolved in methanol (1050 ml) and stirred for one hour to get the clear solution. The solutions was then cooled to 0-5° C. under stirring and maintained at this temperature for two hours. The reaction mass was filtered and dried at 45° C. under vacuum for 5-6 hours to afford the title compound with HPLC purity of 99.49%. This material was re-dissolved in methanol (306 ml) and stirred for one hour at 60-65° C. to get the clear solution. The solution was then cooled to 0-5° C. under stirring and this temperature was maintained for two hours. The solid obtained was filtered and dried at 45° C. under vacuum for 5-6 hours, to yield 47.0 g title compound with HPLC purity of 99.66%.

Step-3: Preparation of Fingolimod free base

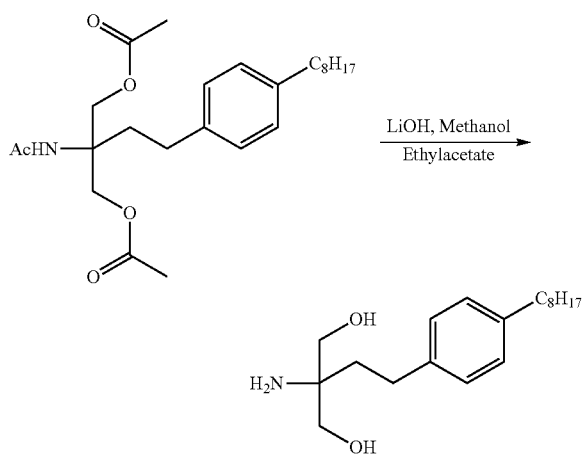

150 g 2-acetamido-2-(4-octylphenethyl)propane-1,3-diyl diacetate and 2250 ml methanol were mixed at room temperature to get the clear solution. LiOH solution (313.0 g LiOH dissolved in 1972.0 ml of DM Water) was then added under stirring to the reaction mixture. Slowly the temperature was raised to reflux and maintained for 4-5 hours. After completion of reaction as confirmed by HPLC, the methanol was concentrated at below 60° c. under full vacuum. The residue was again taken in DM water (750 ml) and the reaction mixture was extracted with ethyl acetate (4.5 lit). Ethyl acetate layer was separated. Aqueous layer was also extracted with ethyl acetate (500 ml). The ethyl acetate layers were combined and washed with saturated sodium chloride soln (750 ml) and DM water (200 ml). Ethyl acetate layer was made moisture free by addition of anhydrous sodium sulfate (250.0 g). After removal of moisture ethyl acetate was recovered at a temperature below 55° C. under full vacuum. When ~500 ml of ethyl acetate is left the reaction mass is cooled to 0-5° C. which is maintained for 2-3 hours. The separated solid is filtered to get 81.0 g Fingolimod free base which is further dried under vacuum at 45° C. for 6-7 hours.

Step 4: Preparation of Fingolimod Hydrochloride

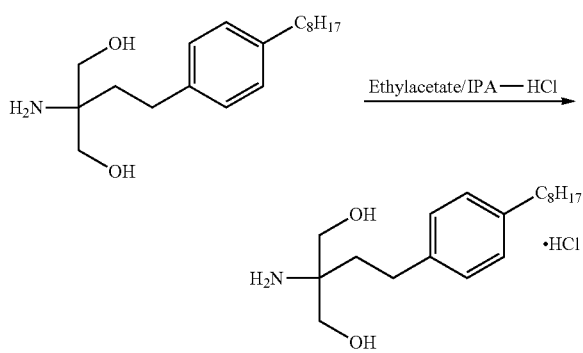

80.0 g Fingolimod free base was charged to 2000 ml ethyl acetate. The reaction mixture was slowly heated up to reflux (~70° C.) to get the clear solution. At the same temperature, 8 g activated Carbon was added to the reaction mass and stirring was done for 20-30 minutes. Reaction material was filtered through celite bed and washed with ethyl acetate (100.0 ml). Mother liquor obtained was heated up to 70° C. to get the clear solution. Then 81.0 ml IPA-HCl (8-10%) was slowly added in 10-15 minutes, while maintaining the pH in between 1-2. The reaction mixture was further stirred for 15-30 minutes at reflux temperature. The reaction temperature was slowly brought to RT naturally and then further cooled to 0-5° C. where it was maintained for 2-3 hours. The separated solid was filtered, washed with ethyl acetate to get the title compound. The material obtained was dried at 45° C. under full vacuum for 6-7 hours to get 80.0 g crystalline Fingolimod hydrochloride characterized by XRPD pattern according to FIG. 1, DSC thermogram substantially according to FIG. 2 and IR spectrum substantially according to FIG. 3.

Purity (By HPLC): 99.83%

Example 2

Preparation of Fingolimod hydrochloride (I)

Step-1: Preparation of 2-acetamido-2-(4-octanoylphenethyl) propane-1,3-diyl diacetate

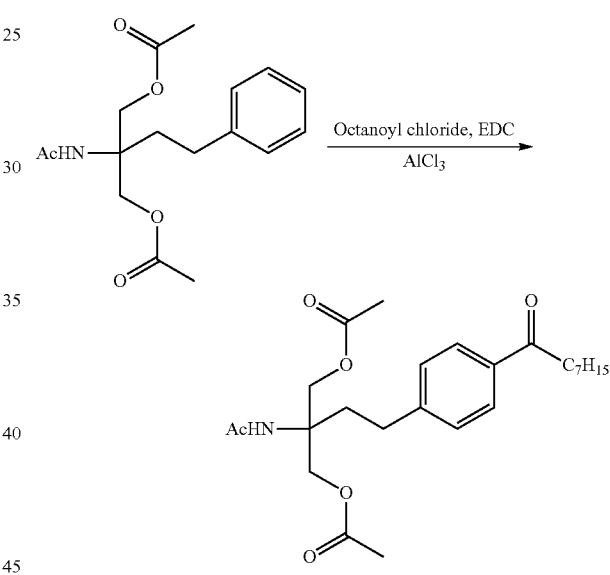

950.0 ml ethylene dichloride (EDC) was charged in to three necked RB flask under nitrogen atmosphere and cooled to 0-5° C. 315 g Aluminum Chloride (AlCl$_3$) was added to the reaction setup and stirred for further 30 minutes under nitrogen atmosphere. Octanoyl chloride (255 ml) was slowly added in to the reaction mixture in one hour at 0° C. under stirring. Then reaction mixture was brought to room temperature and stirred for two hours, followed by cooling to 0-5° C. 95 g 2-acetamido-1,3-diacetoxy-2-(2-phenylethyl) propane dissolved in 285.0 ml EDC was slowly added to the reaction mixture under stirring in duration of two hours maintaining the temperature at 0-5° C. After addition, the reaction mixture was allowed to attain the temperature of 20-25° C. under stirring which was maintained for 14-18 hours. After completion of reaction as monitored by HPLC, reaction mixture was decomposed with chilled water (1900 ml). EDC layer was separated and the aqueous layer was again extracted with EDC (200.0 ml). EDC layer were combined and washed twice with saturated sodium chloride soln. (475 ml). EDC layer was then separated and made moisture free by addition of anhydrous sodium sulfate (50.0 g). EDC layer was recovered under vacuum at temperature below 50° C. to get residue. The obtained residue was further purified by addition of hexane (1738 ml) at room temperature for 1-2 hours to get the solid material, which was further dried at room temperature under vacuum for 6-8 hours to get 83.0 g of the product.

The solid obtained was further purified by column chromatography over silica gel (230-400 mesh). The product was eluted with Ethyl acetate: Hexane (1:1). Appropriate fractions were combined and concentrated to get the residue. Further to this, hexane was added at room temperature to the residue under stirring which was continued for 30 minutes. The solid material was filtered and suck dried for 2-3 hours at room temperature to afford 73.0 g title compound.

Step-2: Preparation of 2-acetamido-2-(4-octylphenethyl) propane-1,3-diyl diacetate

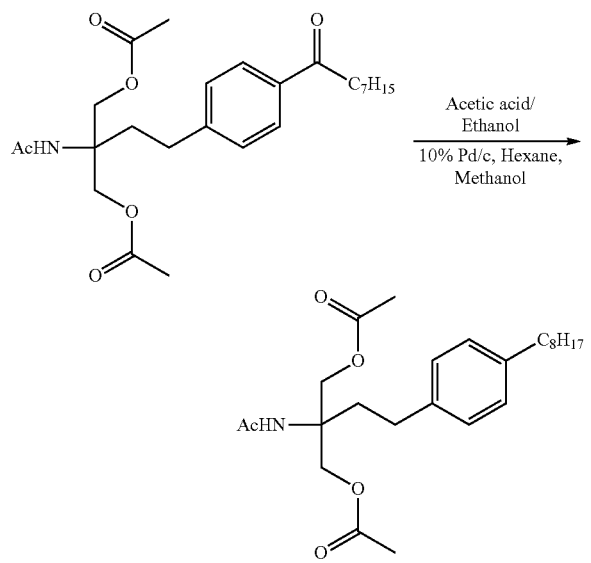

1050.0 ml Ethyl alcohol: Acetic acid (8:2), was charged in Stainless Steel auto clave. 70.0 g of 2-acetamido-2-(4-octanoylphenethyl)propane-1,3-diyl diacetate was then added and stirred for 10-15 mints at room temperature till the solution became clear. This was followed by addition of 7.0 g 10% Pd/C under stirring. After this addition, under stirring Hydrogen gas was applied to the auto clave while maintaining the pressure of 4.0-4.5 kg/cm², at 30-35° C. for 12 hours. After assessing the progress of the reaction by HPLC, the reaction mass was filtered with hyflow bed. The filtrate was then evaporated under full vacuum below 55° C. to get the residue. The residue was added to Hexane (500.0 ml) and stirred for 2-3 hours at 0-5° C. The separated solid material was filtered to afford 59.0 g crude product, after drying at 45-50° C. under vacuum for 4 hours.

The obtained crude title compound was taken in methanol (715 ml) and stirred for 30 minutes to get the clear solution at room temperature. The solution was then cooled to 0-5° C. under stirring which was maintained for two hours. The solid obtained was washed with chilled Methanol (100.0 ml), filtered and dried at 45° C. under vacuum for 2-3 hours, to obtain 42.0 g compound. This 42.0 g material was again dissolved in methanol (252.0 ml) and stirred for one hour to get the clear solution at 40° C. The solutions was again cooled to 0-5° C. under stirring and maintained at this temperature for two hours. The reaction mass was filtered and dried at 45° C. under vacuum for 2-3 hours to afford 37.0 g title compound. This material was re-dissolved in methanol (185.0 ml) and stirred for one hour at 40-45° C. to get the clear solution. The solution was then cooled to 0-5° C. under stirring and this temperature was maintained for two hours. The solid obtained was filtered and dried at 45° C. under vacuum for 2-3 hours, to yield 33.5 g title compound with HPLC purity of 99.53%.

Step-3: Preparation of Fingolimod free base

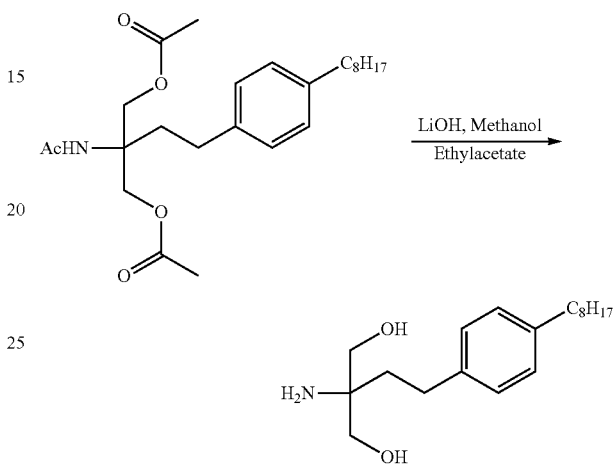

280.0 g 2-acetamido-2-(4-octylphenethyl) propane-1,3-diyl diacetate and 3640.0 ml methanol were mixed at room temperature to get the clear solution. LiOH.H₂O solution (571.2 g LiOH.H₂O dissolved in 3640.0 ml of DM Water) was then added under stirring to the reaction mixture. Slowly the temperature was raised to reflux and maintained for 6-7 hours. After completion of reaction as confirmed by HPLC, the methanol was concentrated at below 55° C. under full vacuum. The residue was again taken in DM water (1400.0 ml) and the reaction mixture was extracted with ethyl acetate (10.0 lit). Ethyl acetate layer was separated. Aqueous layer was again extracted with ethyl acetate (5000.0 ml). The ethyl acetate layers were combined and washed with saturated sodium chloride soln. (1200.0 ml) and DM water (1200.0 ml). Ethyl acetate layer was made moisture free by addition of anhydrous sodium sulfate (1000.0 g). After removal of moisture, ethyl acetate was recovered at a temperature below 45° C. under full vacuum. When ~500 ml of ethyl acetate is left the reaction mass is cooled to 0-5° C. and maintained for 2-3 hours under stirring. The separated solid is filtered to get 210.0 g Fingolimod free base which is further dried under vacuum at 45° C. for 6-7 hours to get 180 g Fingolimod free base. (HPLC Purity: 99.06%)

Step 4: Preparation of Fingolimod Hydrochloride

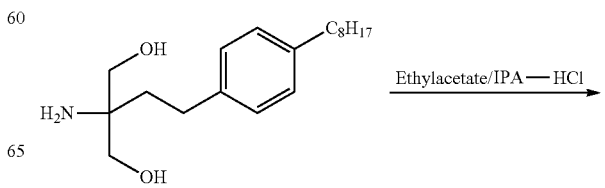

-continued

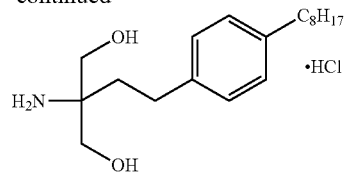

81.0 g Fingolimod free base was charged to 2025.0 ml ethyl acetate. The reaction mixture was slowly heated up to reflux (~70° C.) to get the clear solution. At the same temperature, 8.0 g activated Carbon was added to the reaction mass and stirring was done for 15 minutes. Reaction material was filtered through celite bed and washed with ethyl acetate (20.0 ml). Mother liquor obtained was heated up to 70° C. to get the clear solution. Then 81.0 ml IPA-HCl (8-10%) was slowly added in to the reaction mixture, while maintaining the pH in between 1-2. The reaction mixture was further stirred for 10-15 minutes at reflux temperature. The reaction temperature was slowly brought to room temperature naturally and then further cooled to 0-5° C. where it was maintained for 2 hours. The separated solid was filtered and washed with ethyl acetate (20.0 ml) to get the title compound. The material obtained was dried at 45° C. under full vacuum for 10 hours to get 81.0 g crystalline Fingolimod hydrochloride characterized by XRPD pattern according to FIG. 2, DSC thermogram substantially according to FIG. 3 and IR spectrum substantially according to FIG. 4.

Purity (By HPLC): 99.77%

Example 3

Preparation of Fingolimod hydrochloride (I)

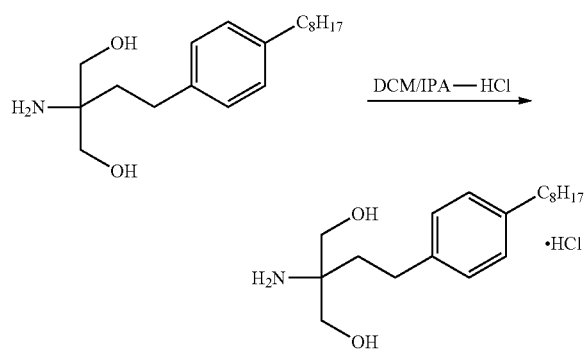

2.0 g Fingolimod free base (as obtained from Step 3 of Example 1) was charged to 80 ml Dichloro methane (DCM). The reaction mixture was slowly heated up to reflux (40° C.) to get the clear solution. At the same temperature, 200 mg activated Carbon was added to the reaction mass and stirring was done for 20-30 minutes. Reaction material was filtered through celite bed and washed with ethyl acetate (10.0 ml).

Mother liquor obtained was heated up to 40° C. to get the clear solution. Then 2.0 ml IPA-HCl (8-10%) was slowly added in 10-15 minutes, while maintaining the pH in between 1-2. The reaction mixture was further stirred for 15-30 minutes at reflux temperature. The reaction temperature was slowly brought to RT naturally and then further cooled to 0-5° C. where it was maintained for 2-3 hours. The separated solid was filtered, washed with DCM to get the title compound. The material obtained was dried at 45° C. under full vacuum for 6-7 hours to get 1.7 g crystalline Fingolimod hydrochloride.

Purity (By HPLC): 99.76%

The invention claimed is:

1. A process for preparing Fingolimod hydrochloride (I), comprising the steps of—
 a) providing a solution of Fingolimod base with an ester or a halohydrocarbon organic solvent used in the range up to more than 20 times (by volume) but less than 50 times (by volume) with respect to weight of Fingolimod free base;
 b) raising the temperature to a range between 35 to 75° C.;
 c) optionally adding activated carbon followed by filtering;
 d) adding 5-10% isopropanol-hydrochloric acid solution; and
 e) isolating the Fingolimod hydrochloride crystalline Form-β;
 the said crystalline Form-β being characterized by x-ray powder diffraction pattern having, characteristic 2θ° peaks in XRPD peak set of 3.54, 7.10, 10.67, 15.36, 17.83, 20.53, 21.49, 23.29, 25.12, 26.68 and 29.22±0.1 2θ°; un-split peak near at 20.5 2θ° and DSC isotherm comprising endothermic peaks selected from peak-1: ranging between 40 to 45° C., peak-2: ranging between 65 to 70° C. and peak-3: ranging between 107 to 115° C.

2. A process for preparing Fingolimod hydrochloride (I) according to claim 1, wherein the Fingolimod hydrochloride obtained as crystalline Form-β is characterized by X-ray powder diffraction pattern comprising characteristic 2θ° peaks in XRPD peak set of 3.54, 7.10, 10.67, 15.36, 20.53, 21.49 and 25.12±0.1 2θ° and DSC isotherm comprising endothermic peaks selected from Peak-1: ranging between 40 to 45° C., Peak-2: ranging between 65 to 70° C. and Peak-3: ranging between 107 to 115° C.

3. A process for preparing Fingolimod hydrochloride (I) according to claim 1, wherein the Fingolimod hydrochloride obtained as crystalline Form-β is further characterized by:
 i. X-ray powder diffraction pattern comprising an un-split peak near at 20.5 2θ°;
 ii. Other characteristic 2θ° peaks selected from the XRPD peak set of 17.83 , 23.29, 26.68 and 29.22±0.1 2θ.

4. A process for preparing Fingolimod hydrochloride (I) according to claim 1, wherein the Fingolimod hydrochloride obtained as crystalline Form-β is further characterized by, particle size distribution of d(0.1): 10-20 μm; d(0.5): 25-35 μm and d(0.9): 45-65 μm.

* * * * *